US00PP08081P

United States Patent [19]

Stravers

[11] Patent Number: Plant 8,081

[45] Date of Patent: Dec. 29, 1992

[54] GERBERA PLANT NAMED TERBARUM

[75] Inventor: Lambertus J. M. Stravers, Kudelstaart, Netherlands

[73] Assignee: Terra Nigra BV, De Kwakel, Netherlands

[21] Appl. No.: 696,598

[22] Filed: May 7, 1991

[30] Foreign Application Priority Data

Nov. 2, 1990 [NL] Netherlands ..... GRB 1172

[51] Int. Cl.[5] ..... A01H 5/00

[52] U.S. Cl. ..... Plt./68.1

[58] Field of Search ..... Plt./68

*Primary Examiner*—James R. Feyrer

*Attorney, Agent, or Firm*—Foley & Lardner

[57] ABSTRACT

A new and distinct cultivar of Gerbera plant named Terbarum, characterized by its single flower type and flat shaped flower form; light orange or cream ray floret color and perianth lobes; green disc florets and small diameter flower head.

1 Drawing Sheet

The present invention comprises a new and distinct cultivar of Gerbera plant, botanically known as *Gerbera jamesonii*, and referred to by the cultivar name Terbarum.

Terbarum was originated from a hybridization made in a controlled breeding program in De Kwakel, The Netherlands in 1988 under the supervision of the inventor Lambertus J. M. Stravers.

The female parent was a cultivar designated M87.391. The male parent was a cultivar designated M89.20. The new cultivar was discovered and selected as one flowering plant within the progeny of the stated parentage by the invention in or about January 1990 in a controlled environment in De Kwakel.

The first asexual reproduction of Terbarum was accomplished when vegetative cuttings were taken from the initial selection in April 1990 in a controlled environment in De Kwakel, The Netherlands by a technician working under formulations established and supervised by the invention. The new cultivar is presently being propagated by cuttings and tissue culture. Horticultural examination of selected units initiated in November 1990 has demonstrated that the combination of characteristics as herein disclosed for Terbarum are firmly fixed and are retained through successive generations of asexual reproduction.

Terbarum has not been observed under all possible environmental conditions. The phenotype may vary significantly with variations in environment such as temperature, light intensity and day length. The following observations, measurements and comparisons describe plants grown in commercial greenhouses in De Kwakel, The Netherlands under controlled conditions which closely typify those generally used in commercial practice.

The following traits have been repeatedly observed and have been determined to be basic characteristics of Terbarum, which in combination provide a new and distinct cultivar:

1. Single type flower and flat shaped flower form.
2. Ray florets are very light orange or cream in color.
3. Green disc florets.
4. Perianth lobe is also light orange in color.
5. The diameter of the flower head is small, approximately 65 mm.

Of the many commercial cultivars known to the present inventor, certain comparisons can be made with the new cultivar. The new cultivar Terbarum has a relatively small flower diameter and is similar in this characteristic, and also growth habit, to the cultivars Terkapol, Tertala and Terikatir, all cultivars of the present inventor disclosed in pending plant patent applications. However, Terbarum differs from the other cultivars in flower color and certain other characteristics. The flower color of Terbarum, a very light orange or cream, is somewhat similar to the flower color of the cultivar Terfacci which, however, is slightly darker. A further difference is that Terfacci has a much larger flower diameter of 10–11 cm.

In comparison to the parent cultivars, the female parent M 87.391 has semi-double flower type, flat flower form, purple ray florets, green disc florets, and a much greater diameter of 80–90 mm. The male parent M89.20 has semi-double flower type and flat flower form, pink ray florets and purple disc florets, and a flower diameter of 60–69 mm.

The accompanying photographic drawing shows typical inflorescence characteristics of Terbarum, with the colors being as nearly true as possible with illustrations of this type.

In the following description, color references are made to The Royal Horticultural Society Colour Chart (R.H.S.). The color values were determined at approximately 9:30 a.m. on Feb. 20, 1991 under natural light at De Kwakel, The Netherlands.

Classification:

*Botanical.*—*Gerbera jamesonii* cv Terbarum.

*Commercial.*—Gerbera.

Parentage: Seedling from cross of 87.391 and M89.20.

Plant: The plant when fully grown after approximately five (5) months of growth reaches a height of 35 cm, measured from the soil line.

Leaf blade:

*Length.*—Short.

*Width.*—Narrow.

*Blistering (puckering).*—Medium.

*Hairiness on upper side.*—Medium.

*Depth of cuts or incisions.*—Strong in central part of leaf.

*Color.*—Upper surface of leaf 137A, medium green; lower surface 138A.

*Glossiness on upper side.*—Weak.

*Angle at tip.*—Acute.

*Shape at tip.*—Pointed.
*Margin of lobes.*—Serrate.
*Extension of margin.*—Small.
*Petiole length.*—Medium.
*Petiole anthocyanin coloration.*—Present, medium in intensity.

Peduncle:
*Length.*—Short.
*Cross section.*—Round, medium strength and thickness.
*Hairiness.*—Medium.
*Color.*—Medium green.
*Anthocyanin.*—Present at base, medium in intensity, none present at tip.
*Bracts.*—Absent.

Flower head:
*Type.*—Single; flat shaped in form.
*Diameter from edge to edge.*—Approximately 65 mm; varies somewhat depending on season and stage of development.
*Involucre.*—Height: Medium. Diameter: Small. Bracts: Longitudinal axis on inner rows are straight. Anthocyanin: Absent.
*Ray florets.*—Number in outer row: 40–60. Length of floret: Less than 29 mm. Width of floret: 5–9 mm. Shape of floret: Generally elliptical with narrow base; longitudinal folding is strong. Shape of tip: Rounded, angle obtuse, two incisions, shallow in depth. Cross section of floret: Flat. Color distribution on inner side: Uniform. Striation: Absent. Claw spot: Absent. Color on top side: 27D. Color on bottom side: 19D. Color (general tonality from a distance of 3 meters: Very light orange.
*Disc florets.*—Diameter: 10–19 mm. Main color of perianth lobes: Light cream. Color (mature and immature): Green.

Reproductive parts:
*Stigma.*—Main color, white.
*Anthers.*—Main color, yellow; anthocyanin coloration absent.
*Pappus.*—Main color, green.
*Style.*—Main color of distal part is white.

Disease Resistance: Medium.
Pest Resistance: Medium.

I claim:

1. A new and distinct cultivar of Gerbera plant named Terbarum, as illustrated and described.

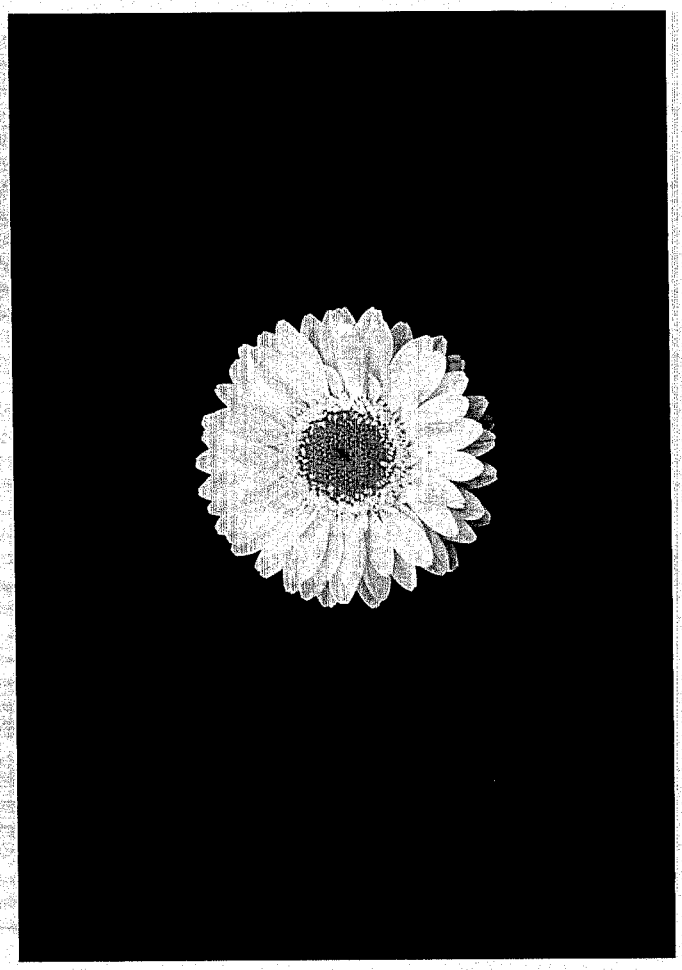

* * * * *